(12) United States Patent
Hsu et al.

(10) Patent No.: US 9,308,154 B2
(45) Date of Patent: Apr. 12, 2016

(54) METHOD FOR PRODUCING ELASTIC VESICLES

(71) Applicant: Greenjoy Biotech Co., Ltd., Taichung (TW)

(72) Inventors: Jaw-Cherng Hsu, Taichung (TW); Ying-Hsuan Wu, Hsinchu (TW)

(73) Assignee: Greenjoy Biotech Co., LTD., Taichung (TW)

(*) Notice: Subject to any disclaimer, the term of this patent is extended or adjusted under 35 U.S.C. 154(b) by 0 days.

(21) Appl. No.: 14/310,328

(22) Filed: Jun. 20, 2014

(65) Prior Publication Data

US 2015/0098986 A1    Apr. 9, 2015

(30) Foreign Application Priority Data

Oct. 9, 2013  (TW) .............................. 102136560 A

(51) Int. Cl.
    *A61K 8/14*         (2006.01)
    *A61K 9/127*       (2006.01)
    *A61Q 19/00*       (2006.01)

(52) U.S. Cl.
    CPC . *A61K 8/14* (2013.01); *A61Q 19/00* (2013.01); *A61K 9/1272* (2013.01); *A61K 2800/10* (2013.01); *A61K 2800/412* (2013.01); *A61K 2800/805* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

2004/0033303 A1*   2/2004   Landon .................... 426/581
2008/0274195 A1*  11/2008  Nicolosi et al. ............ 424/489
2008/0305055 A1*  12/2008  Baschong et al. ........... 424/59

OTHER PUBLICATIONS

YF Maa, CC Hsu. "Performance of Sonication and Microfluidization for Liquid—Liquid Emulsification." Pharmaceutical Development and Technology, vol. 4(2), 1999, pp. 233-240.*
Y-H Wu, J-C Hsu. "The mechanical property and transport ability of caffeine's transfersome." Graduate Institute of Cosmetic Science, Hungkuang University, 2012, pp. 1-12.*
CD Pirvu, C Hlevca, A Ortan, R Prisada. "Elastic Vesicles as Drugs Carriers Through the Skin." Farmacia, vol. 58 No. 2, 2010, pp. 128-135.*

* cited by examiner

*Primary Examiner* — Isaac Shomer
(74) *Attorney, Agent, or Firm* — Tracy M. Heims; Apex Juris, pllc.

(57) ABSTRACT

A method for producing elastic vesicles enveloping active ingredients includes pre-emulsification of a formulation of elastic vesicles and a homogenization step. The pre-emulsification of a formulation of elastic vesicles includes heating and uniformly mixing water phase of the formulation and active ingredients until the active ingredients completely dissolve in the water, and adding an oil phase of the formulation premixed with edge activators to accomplish the pre-emulsification. The homogenization step includes using a device for miniaturizing or nanometerizing particles to proceed with disruption and homogenization.

13 Claims, 3 Drawing Sheets

(a) PC (b) EA (c)

(d)

METHOD FOR PRODUCING ELASTIC VESICLES

BACKGROUND OF THE INVENTION

The present invention relates to a method for producing elastic vesicles and, more particularly, to a method for producing elastic vesicles for enveloping active ingredients of cosmetics.

Active ingredients with alleged special effects have been added into formulations as the techniques of skin care products evolve. However, it is still a problem whether these active ingredients can successfully enter the deep layers of human skin and act in the target area. Transdermal drug delivery systems are techniques permitting a drug to penetrate the skin to achieve effective concentration, which, when applied in development of cosmetics, can increase the penetrating speed and amount of the active ingredients of the skin care products. Commonly used methods include sonophoresis, iontophoresis, and vesicle enveloping technique. A liposome is one of vesicles and is a micro particle comprised of phospholipids. Since phospholipids are amphipathic molecules that will self-assembly into an aggregate when they reach the critical micellar concentration (CMC) in a polar solvent having a better hydrophilicity, and phospholipids have a lipid bilayer to effectively envelope the active ingredients while possessing excellent biofilm permeability. Thus, they are widely used in a vesicle enveloping technique. This technique was found in 1965 by Alec Bangham of Babraham Institute. Liposomes were for the first time accepted as vesicles for drugs in 1970, and animal tests were conducted. Amphotericin B (a liposome drug) was accepted to cure general fungal infection in Ireland in 1990. In 1995, the Food and Drug Administration of the U.S. approved Liposomal Doxorubicin to the market.

Research showed that liposomes are compatible with skin and tissues without causing allergy. Furthermore, liposomes can degrade into phospholipids and turn into a portion of the cell membrane. However, liposomes have two drawbacks. Firstly, liposomes have a large diameter and, thus, can only act on the upper layer of the corneum rather than penetrating the granular layer of the epidermis, leading to an increase in the amount of the active ingredients stagnant on the skin and, hence, failing to achieve effective absorption. Secondly, both research of Kirjavainen in 1999 and research of Fang et al. in 2001 showed that the active ingredients are less impotent in penetrating the skin when the structure of the liposome is more stable. According to the previous research results, liposomes lack elasticity and, thus, cannot penetrate the gap in the epidermal layer because the lipid bilayer structure is rigid.

Elastic vesicles, which are a special liquid transdermal drug vesicle and are different from conventional liposomes, were published in early 1990 for the first time. Elastic vesicles essentially consists of phosphatidylcholine (PC) and edge activators (EA). Phosphatidylcholine is the essential component of the vesicle. The edge activators provide the lipid bilayer membranes of the elastic vesicles with flexibility during production of the elastic vesicles.

Phosphatidylcholine is the essential component of a biofilm and consists of a hydrophilic polar head group formed by phosphoryl groups and two hydrophobic fatty acid chains. When the molecules of phospholipids disperse in water, the molecules self-assemble into a concentric ball structure due to the difference in the hydrophilicity and hydrophobicity at two ends. The water soluble substances are enveloped, and the fat soluble substances are embedded on the surfaces of the elastic vesicles. Edge activators, also referred to as "surfactants", include both hydrophilicity and lipophilicity. The lipophilic groups generally consist of long-chain hydrocarbon radicals having small structural differences. There are more types of hydrophilic groups and, thus, having larger differences therebetween. Generally, single-chain surfactants having larger radiuses of curvatures are selected for the purpose of increasing the flowability in the lipid bilayer to improve the deformability and permeability, such that the elastic vesicles are highly deformable to penetrate through skin pores having a size much smaller than the elastic vesicles. Thus, the release of drugs can be prolonged, and the activity of the drugs can be enhanced through transdermal penetration.

Elastic vesicles can be applied in various drugs, including non-steroidal anti-inflammatory drugs, analgesics, insulin, anaesthetics, anti-malarial drugs, anti-cancer drugs, and melatonin. Elastic vesicles are suitable to hydrophilic and lipophilic drugs and possess biocompatibility and biodegradability. Since the structure of elastic vesicles is similar to that of natural phospholipids, the elastic vesicles can effectively prolong the release of drugs and reduce the half-life of drugs. Thus, it is a drug administration system worth developing. However, research of application of the elastic vesicles in the cosmetic field are few. If the elastic vesicles are applied to envelope the active ingredients, it will be a novel, promising technique.

However, production of elastic vesicles requires addition of organic solvents, and the safety of production is questioned. As an example, the research result published by Cevc and Blume in 1992 showed that preparation of elastic vesicles required dissolving phosphatidylcholine and edge activators with chloroform and methyl alcohol (which are organic solvents) at a ratio of 2:1, and the organic solvents were subsequently removed by rotary evaporation. However, residue of the organic solvents was still possible.

BRIEF SUMMARY OF THE INVENTION

A method for producing elastic vesicles enveloping active ingredients according to the present invention includes:

pre-emulsification of a formulation of elastic vesicles: including heating and uniformly mixing water of a water phase of the formulation and active ingredients until the active ingredients completely dissolve in the water, and adding an oil phase of the formulation premixed with edge activators to accomplish the pre-emulsification; and a homogenization step including using a device for miniaturizing or nanometerizing particles to proceed with disruption and homogenization.

In an example, the homogenization step includes placing the pre-emulsified elastic vesicles into a nano high-pressure homogenizer to proceed with homogenization for 1-15 times, with the nano high-pressure homogenizer conducting the homogenization at a pressure between 0 and 1500 bar, and with the homogenizer including a cooling tank operating at a temperature between 0 and 80 Celsius degrees.

In another example, the homogenization step includes using an ultrasonic oscillation method.

The active ingredients can include substances for losing weight, whitening, anti-oxidation, anti-aging, or activating metabolism of cells.

The oil phase can include silicon-containing edge activators, anionic edge activators, cationic edge activators, amphionic edge activators, and nonionic edge activators.

The oil phase can include phosphatidylcholine and silicon-containing edge activators, and a weight ratio of the silicon-containing edge activators is 10%-20% per weight unit.

The present invention will become clearer in light of the following detailed description of illustrative embodiments of this invention described in connection with the drawings.

DETAILED DESCRIPTION OF THE INVENTION

An objective of the present invention is to reduce the disadvantages of elastic vesicles, and a high pressure homogenization step is used to replace the thin-film hydration method using organic solvents to produce elastic vesicles. This method reduces the safety risks. In preparation of the elastic vesicles, a silicon-containing emulsifier (see Table 1) is used as an edge activator to increase the entrapment efficiency and the penetrability. Nine formulation compositions were provided according to differing ratios, and the names and ratios are shown in Table 2.

The method for producing elastic vesicles enveloping active ingredients according to the present invention includes:

pre-emulsification of a formulation of elastic vesicles: including heating and uniformly mixing water of a water phase of the formulation and active ingredients until the active ingredients completely dissolve in the water, and adding an oil phase of the formulation premixed with edge activators to accomplish the pre-emulsification; and a homogenization step including using a device for miniaturizing or nanometerizing particles to proceed with disruption and homogenization.

The homogenization step includes placing the pre-emulsified elastic vesicles into a nano high-pressure homogenizer to proceed with homogenization for 1-15 times, with the nano high-pressure homogenizer conducting the homogenization at a pressure between 0 and 1500 bar, and with the homogenizer including a cooling tank operating at a temperature between 0 and 80 Celsius degrees.

The homogenization step includes using an ultrasonic oscillation method.

The active ingredients include substances for losing weight, whitening, anti-oxidation, anti-aging, or activating metabolism of cells.

The oil phase includes silicon-containing edge activators, anionic edge activators, cationic edge activators, amphionic edge activators, and nonionic edge activators.

The oil phase includes phosphatidylcholine and silicon-containing edge activators, and a weight ratio of the silicon-containing edge activators is 10%-20% per weight unit.

Figure 1:
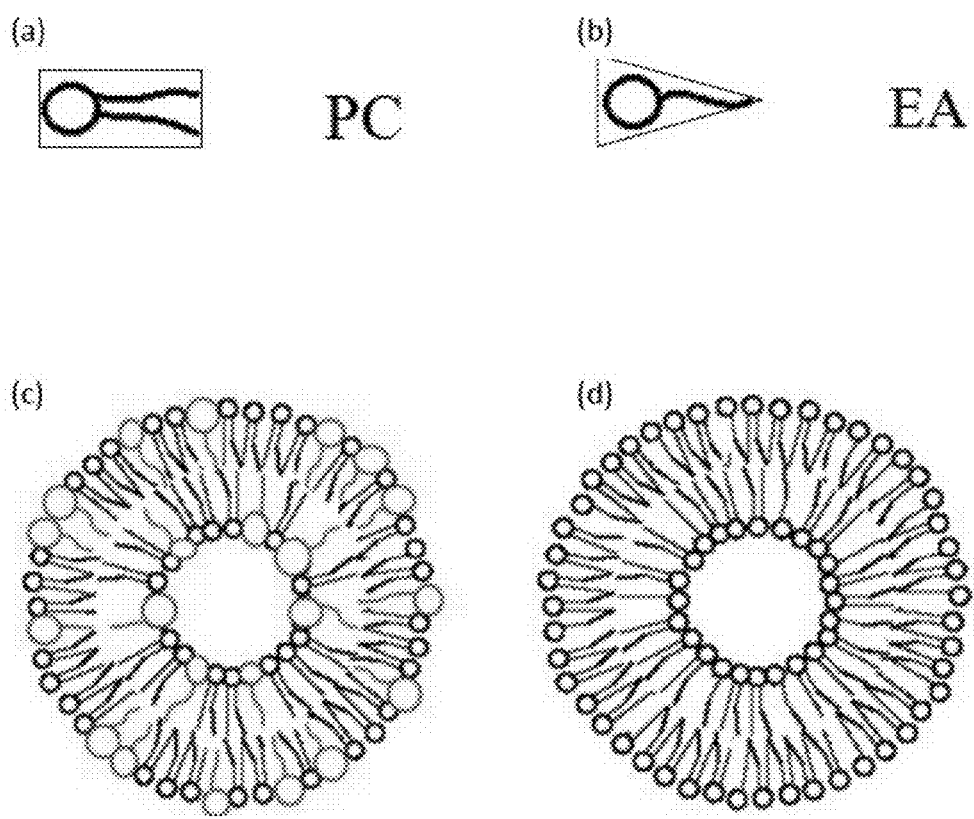
FIG. 1 shows a structural diagram of a liposome and an elastic vesicle.

FIG. 1 shows a structural diagram of a liposome and an elastic vesicle. FIG. 1(a) shows the structure of phosphatidylcholine (PC). It includes two lipophilic carbon chains, represents a parallelepiped, and has a compact structure. FIG. 1(b) shows the structure of an edge activator (EA). It includes a lipophilic carbon chain, represents a triangular pyramid, and has gaps. FIG. 1(c) shows the structure of an elastic vesicle. FIG. 1(d) is a liposome.

Figure 2:
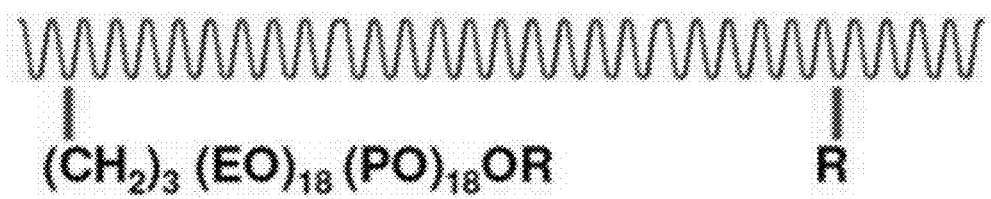
FIG. 2 shows a formulation of an example according to the present invention.
Figure 3:
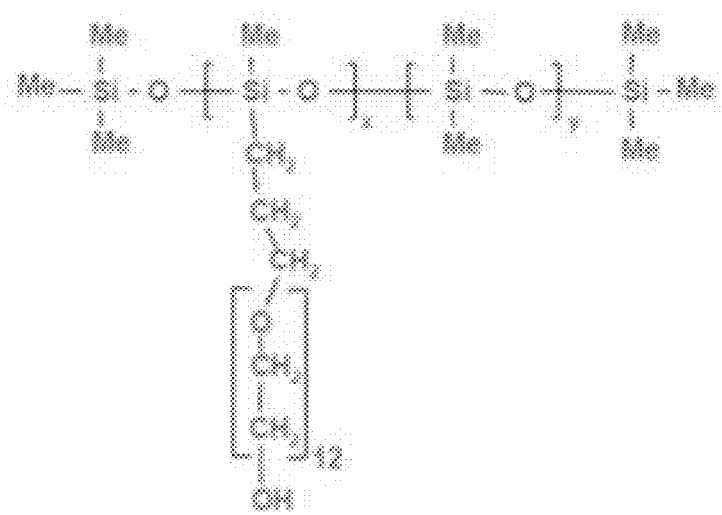
FIG. 3 shows a formulation of another example according to the present invention.
Figure 4:
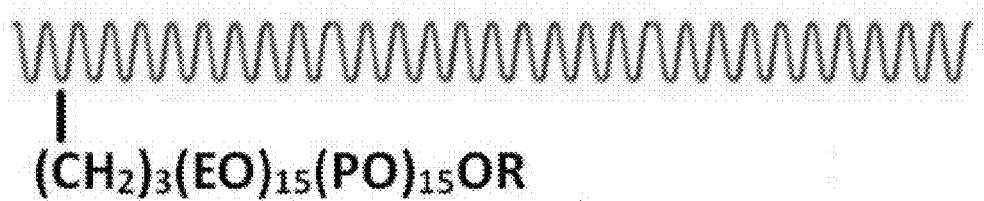
FIG. 4 shows a formulation of a further example according to the present invention.

With reference to FIGS. 2-4 showing an example of the present invention, to increase the elastic effect of the lipid bilayer, phospohatdylcholine was used to combine with silicon-containing edge activators having differing HLB values as the formulations for producing elastic vesicles. Due to the angle between the bonds, the silicon-containing edge activators are more permeable to air, are more stable, and have a better intermiscibility with silicon oils and lipids. Due to the different ratio of the hydrophilic groups to the hydrophobic groups, the HLB values of three silicon-containing edge activators were different. The lower the HLB value is, the more hydrophilic the silicon-containing edge activator is. Furthermore, triglyceride (CCTG) was added as the oil phase of the formulation. 1,3-butylene glycol was used as a solubilizer. Caffeine was the active ingredient to be enveloped. The intended purpose of caffeine was only for losing weight. The active ingredients to be enveloped can be varied according to different needs.

TABLE 1

Silicon-Containing Edge Activators

| INCI Name | Trade name | HLB |
| --- | --- | --- |
| lauryl PEG/PPG-18/18 methicone | 5200 Formulation Aid | 2.2 |
| PEG-12 dimethicone | 193C Fluid | 12.2 |
| PEG/PPG-15/15 dimethicone | 5330 Fluid | 7.1 |

TABLE 2

Reference Table for 9 Formulation Samples of Silicon Elastic Vesicles

| Trade name (INCI) | PC:EA (w/w) | Code of formulation |
| --- | --- | --- |
| 5200 Formulation Aid | 90:10 | LP-18M-1 |
| (lauryl PEG/PPG-18/18 | 85:15 | LP-18M-2 |
| methicone, or LP-18M) | 80:20 | LP-18M-3 |
| 5330 Fluid | 90:10 | P-15D-1 |
| (PEG/PPG-15/15 dimethicone, | 85:15 | P-15D-2 |
| or P-15D) | 80:20 | P-15D-3 |
| 193C Fluid | 90:10 | P-12D-1 |
| (PEG-12 dimethicone, or P-12D) | 85:15 | P-12D-2 |
| | 80:20 | P-12D-3 |

To replace the thin-film hydration method for producing elastic vesicles, in an example of the present invention, the first step was pre-emulsification of a formulation (FIG. 2) of elastic vesicles. The water of the water phase of the formulation was mixed with the active ingredients to be enveloped. The active ingredients included substances for losing weight, whitening, anti-oxidation, anti-aging, or activating metabolism of cells. Water and the active ingredients to be enveloped were mixed and heated to a homogeneous state until the active ingredients completely dissolved in the water. Then, an oil phase of the formulation premixed with edge activators was added after the temperature was lowered. The oil phase was phosphatidylcholine, silicon-containing edge activators, and 1,3-butylene glycol (the formulations were shown in Tables 3-6). The solution was stirred with a glass rod to a homogeneous state and then stirred with a stirrer at 500 rpm for 1 minute. Then, triglyceride was added into the solution, the speed was increased to 1000 rpm, and the stirring maintained for 1 minute. After reaching the homogenous state, the water phase was added slowly, the speed was increased to 2000 rpm, and the stirring maintained for 2 minutes. Lastly, germaben-2 was added, and the solution was stirred for 1 minute. The pre-emulsification was, thus, completed.

The second step was a homogenization step including using a device for miniaturizing or nanometerizing particles to proceed with disruption and homogenization. In this example, a nano high-pressure homogenizing method was used to proceed with disruption and homogenization. However, the homogenization step can include using an ultrasonic oscillation method. In this example, a nano high-pressure homogenizer was used, and the number of passes (N) was 4-8 (preferably 6). The nano high-pressure homogenizer conducted the homogenization at a pressure (P) of 250-750 bar (preferably 500 bar). The nano high-pressure homogenizer includes a cooling tank operating at a temperature of 4-20 Celsius degrees (preferably 16 Celsius degrees). The homogenous step can use an ultrasonic oscillation method. Finally, a laser scattering meter was used to measure the average particle sizes and polydispersity index (PDI).

The phospholipids in the oil phase of the formulation include, but not limited to, phosphatidylcholine (PC), phosphatidylinostiol (PI), phosphatidyethanolamine (PE), and phosphatidic acid (PA), which are the essential components of biofilms.

The edge activators in the oil phase of the formulation included silicon-containing edge activators, anionic edge activators, cationic edge activators, amphionic edge activators, and nonionic edge activators. The silicon-containing edge activators included, but not limited to, lauryl PEG/PPG-18/18 methicone, and PEG-12 dimethicone, PEG/PPG-15/15 dimethicone. The anionic edge activators included sodium lauryl sulfate, sodium lauryl ether sulfate, and disodium lauryl sulfosuccinate. The cationic edge activators included cetyl trimethyl ammonium chloride and alkyl dimethyl benzyl ammonium chloride. The amphionic edge activators included cocoamidopropyl betaine and sodium cocoamphoacetate. The nonionic edge activators included cocamide MEA, polysorbate 80, sorbitan monostearate, and steareth-2.

The behnyl alcohol in the oil phase of the formulation included, but not limited to, propylene glycol, glycerine, 1,3-butylene glycol, sorbitol, and polyethylene glycol, all of which could be used as solubilizers.

The neutral lipids in the oil phase of the formulation included, but not limited to, caprylic/capric triglyceride, isopropyl palmitate, and isostearyl isostearate.

The preservatives in the formulation included, but not limited to, germaben-2 (propylene glycol, diazolidinyl urea, methylparaben, propylparaben), methyl paraben, phenoxyethanol, and triclosan.

TABLE 3 formulation abbreviations

| abbreviations of ingredients |
|---|
| PC (phosphatidylcholine) |
| EA (lauryl PEG/PPG-18/18 methicone, or LP-18M; PEG-12 dimethicone, or P-12D; PEG/PPG-15/15 dimethicone, or P-15D) |
| 1,3-BG (1,3-butylene glycol) |
| CCTG (caprylic/capric triglyceride) |
| Water (D.I. water) |
| Caffeine ($C_8H_{10}N_4O_2$) |
| Germaben-2 (propylene glycol, diazolidinyl urea, methylparaben, propylparaben) |

TABLE 4

Formulations of LP-18M Elastic Vesicles

| | Name | | |
|---|---|---|---|
| formulation | LP-18M-1 (100 g) | LP-18M-2 (100 g) | LP-18M-3 (100 g) |
| PC | 1.8 | 1.7 | 1.6 |
| LP-18M | 0.2 | 0.3 | 0.4 |
| 1,3-BG | 10 | 10 | 10 |
| CCTG | 10 | 10 | 10 |
| caffeine | 2 | 2 | 2 |
| water | 75.5 | 75.5 | 75.5 |
| Germaben-2 | 0.5 | 0.5 | 0.5 |

TABLE 5

Formulations of P-15D Elastic Vesicles

| | Name | | |
|---|---|---|---|
| formulation | P-15D-1 (100 g) | P-15D-2 (100 g) | P-15D-3 (100 g) |
| PC | 1.8 | 1.7 | 1.6 |
| P-15D | 0.2 | 0.3 | 0.4 |
| 1,3-BG | 10 | 10 | 10 |
| CCTG | 10 | 10 | 10 |
| caffeine | 2 | 2 | 2 |
| water | 75.5 | 75.5 | 75.5 |
| Germaben-2 | 0.5 | 0.5 | 0.5 |

TABLE 6

Formulations of P-12D Elastic Vesicles

| | Name | | |
|---|---|---|---|
| formulation | P-12D-1 (100 g) | P-12D-2 (100 g) | P-12D-3 (100 g) |
| PC | 1.8 | 1.7 | 1.6 |
| P-12D | 0.2 | 0.3 | 0.4 |
| 1,3-BG | 10 | 10 | 10 |
| CCTG | 10 | 10 | 10 |
| caffeine | 2 | 2 | 2 |
| water | 75.5 | 75.5 | 75.5 |
| Germaben-2 | 0.5 | 0.5 | 0.5 |

The above description recites application of the high-pressure homogenous method and the silicon-containing emulsifiers. However, the present invention is not limited to these operating conditions.

Nine elastic vesicles were prepared by the above elastic vesicle formulations and techniques, and high-performance liquid chromatography (HPLC) was used to proceed with analysis. The injected volume was 20 μL. The detection wavelength was 275 nm. The mobile phase was flushed with water at a flow rate of 1.0 mL/min. The amount of inputted sample was 20 μL. μL. 5-100 ppm caffeine standard solution was used to create a calibration curve. Each concentration was detected three times to obtain the average value. Peak-ABC Chromatography Data Handling System (manufactured by Great Tide Instruments, Taiwan) was used to capture and handle the signals.

As can be seen from Table 7, the edge activators with different HLB values having the three highest entrapment efficiencies were P-12D-1 (60.67%), P-15D-3 (59.27%), and LP-18M-2 (51.02%).

TABLE 7

Entrapment Efficiency of 7 Elastic Vesicles

| Elastic vesicles | Entrapment efficiency (%) |
|---|---|
| LP-18M-1 | 49.41 |
| LP-18M-2 | 51.02 |
| LP-18M-3 | 43.00 |
| P-15D-1 | 58.72 |
| P-15D-2 | 57.69 |
| P-15D-3 | 59.27 |
| P-12D-1 | 60.67 |
| P-12D-2 | 58.26 |
| P-12D-3 | 54.92 |

With regard to measurement of elasticity, filter papers were used as the membranes of the vesicles. Specifically, 0.5 mL of an elastic vesicle was placed on a penetration membrane. Time counting was started when the liquid contacted the filtering membrane. The time of the first drop appeared below the filtering membrane was recorded, and relative deformability, the unit of which is second (s), was defined. After penetration of all of the samples was completed, the average speeds (ml/s) were obtained by the time record. Then, the time evaluating function for the elasticity (E) could be calculated and used as a parameter for measurement of elasticity. Each measurement was conducted three times to obtain the average value.

As can be seen from Table 8, three silicon-containing edge activators had higher relative deformability under three ratio conditions. The relative deformability and deforming speed of LP-18M-1 were 21.00±2.00 s and 0.010 ml/s, respectively. The relative deformability and deforming speed of LP-18M-2 were 18.33±0.58 s and 0.007 ml/s, respectively. The relative deformability and deforming speed of LP-18M-383 were 17.67±2.08 s and 0.008 ml/s, respectively. P-15D had the fastest relative deformation. The relative deformability and deforming speed of P-15D-1 were 14.33±1.53 s and 0.010 ml/s, respectively. The relative deformability and deforming speed of P-15D-2 were 13.00±1.00 s and 0.009 ml/s, respectively. The relative deformability and deforming speed of P-15D-3 were 11.67±1.53 s and 0.010 ml/s. P-12D had middle performance. The relative deformability and deforming speed of P-12D-1 were 14.67±2.08 s and 0.010 ml/s, respectively. The relative deformability and deforming speed of P-12D-2 were 14.33±4.16 s and 0.010 ml/s, respectively. The relative deformability and deforming speed of P-12D-3 were 14.33±3.06 s and 0.009 ml/s, respectively.

TABLE 8

Relative Deformation and Deforming Speed of 9 Elastic Vesicles

| Elastic vesicles | Relative deformability (s) | Deforming speed (ml/s) |
|---|---|---|
| LP-18M-1 | 21.00 ± 2.00 | 0.010 |
| LP-18M-2 | 18.33 ± 0.58 | 0.007 |
| LP-18M-3 | 17.67 ± 2.08 | 0.008 |
| P-15D-1 | 14.33 ± 1.53 | 0.010 |
| P-15D-2 | 13.00 ± 1.00 | 0.009 |
| P-15D-3 | 11.67 ± 1.53 | 0.010 |
| P-12D-1 | 14.67 ± 2.08 | 0.010 |
| P-12D-2 | 14.33 ± 4.16 | 0.010 |
| P-12D-3 | 14.33 ± 3.06 | 0.009 |

With regard to in vitro transdermal delivery analysis, pretreatment before the experiments were carried out. An ear skin was prepared and cleaned with secondary water. The upper skin of the pig ear was cut by a scalpel to remove the fat layer. Then, the pig ear was cut into a plurality of penetration membranes each having an area of 1.5×1.5 cm$^2$ and each having a thickness of 605 μm. The penetration membranes were soaked in phosphate buffer saline (PBS), were sealed in a bag, and were frozen at 4° C. for future use.

Figure 5:
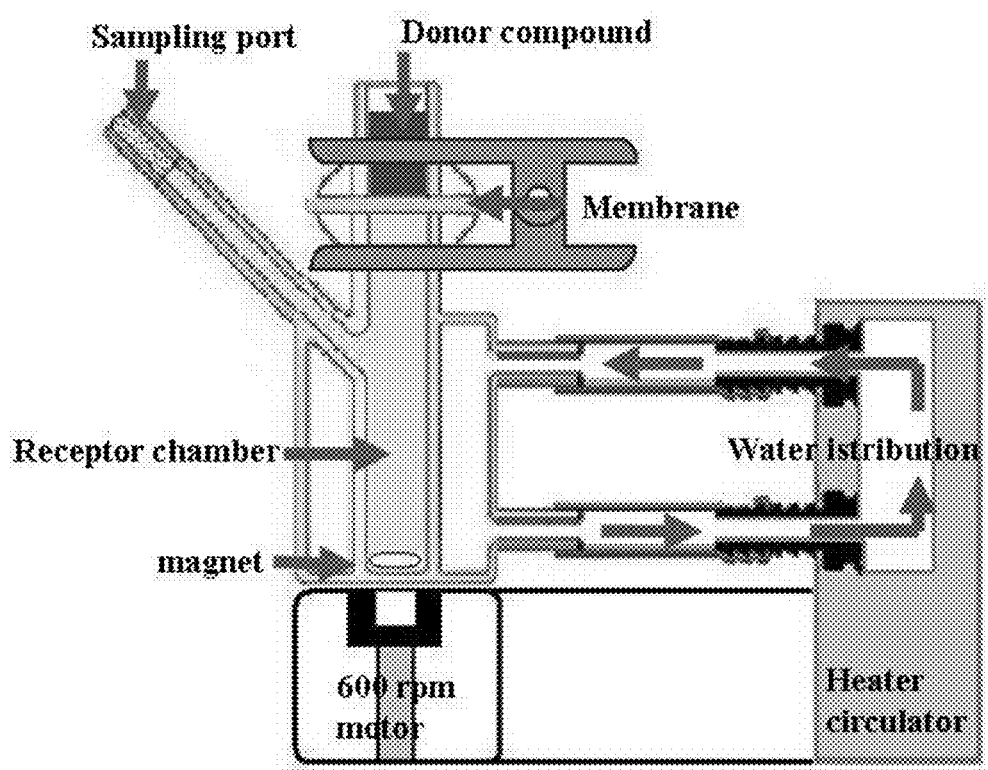
FIG. 5 is a diagram of a device for carrying out a method for producing elastic vesicles according to the present invention.

With reference to FIG. 5, in the beginning of the experiment, the penetration membranes were unfrozen in PBS to room temperature, such that the gaps between the keratinocyte cells returned to their natural state. The penetration membranes were fixed in a Franz-type diffusion cell (the diffusion area was 0.636 cm$^2$). To test the skin integrity, the upper and lower sections of the diffusion cell were filled with PBS. After removing bubbles from the lower chamber, a penetration membrane was proved to be intact if the resistance between two sides of the penetration membrane was larger than 4 kΩ.

A sample of 1.0 mL was placed into the upper, donor cell, and PBS was placed into the lower, receptor cell having a volume of 5.3 mL. A thermostat water tank heater was used to control the water temperature to be 35° C.±1. Stirring was carried out by using a magnet to balance the drug concentration distribution in the receptor cell.

Each experiment used 5 diffusion cells to obtain the average value. 50 μL was sampled from the receptor cell and analyzed by HPLC. The same amount of a physiological solution was filled back into the receptor cell to maintain the total volume in the receptor cell. The experiment lasted 6 hours.

Table 9 shows the results after calculation. The 6$^{th}$-hr total penetrations of P-15D-3 elastic vesicle, LP-18M-2 elastic vesicle, and P-12D-1 elastic vesicle were 2.43 mg/cm$^2$, 1.85 mg/cm$^2$, and 1.32 mg/cm$^2$, respectively. The flux of P-15D-3 elastic vesicle, LP-18M-2 elastic vesicle, and P-12D-1 elastic vesicle were 0.43, 0.33, and 0.24, respectively. With regard to lag-time, P-15D-3 elastic vesicle was 0.46 hr, LP-18M-2 elastic vesicle was 0.76 hr, and P-12D-1 elastic vesicle was 0.76 hr. With regard to penetration coefficient, P-15D-3 elastic vesicle was 0.022 cm/hr, LP-18M-2 elastic vesicle was 0.017 cm/hr, and P-12D-1 elastic vesicle was 0.012 cm/hr.

TABLE 9

| Elastic vesicle | 6$^{th}$-hr total penetration (mg/cm$^2$) | Flux (mg/cm$^2$ · hr) | Lag time (s) | Penetration coefficient (kp) (cm/hr) |
|---|---|---|---|---|
| P-15D-3 | 2.43 | 0.43 | 0.46 | 0.022 |
| LP-18M-2 | 1.85 | 0.33 | 0.76 | 0.017 |
| P-12D-1 | 1.32 | 0.24 | 0.76 | 0.012 |

According to the test results, the particle sizes of the elastic vesicles were in a range of 164.0-174.4 nm, which were far smaller than the pores of the skin of a human body. The entrapment efficiency was 43.00-60.67%. The relative deformability was 11.67-21.00 s. The deforming speed was 0.007-0.010 ml/s. The 6$^{th}$-hr total penetration was 1.32-2.43 mg/cm$^2$. The flux was 0.24-0.43 mg/cm$^2$·hr. The lag time was 0.46-0.76 s. The penetration coefficient (kp) was 0.12-0.22 cm/hr.

The optimal particle size was 164.0-170.2 nm. The entrapment efficiency was 54.92-60.67%. P-15D edge activators had good performance in both of the optimal particle size and the entrapment efficiency. With regard to the elasticity and the in vitro transdermal delivery of the elastic vesicles produced from three silicon-containing edge activators, the performance of P-15D-3 was better than the other two elastic vesicles in the relative deformability (11.67 s), the deforming speed (0.010 ml/s), the 6$^{th}$-hr total penetration (2.43 mg/cm$^2$), the flux (0.43 mg/cm$^2$·hr), the lag time (0.46 s), and the penetration (0.22 cm/hr). The overall performance of LP-18M was not good, and the reason could be its low HLB (it is a high hydrophobic edge activator). The drugs entrapped in the experiments were hydrophilic. The LP-18M elastic vesicles caused reduction in the temporary hydropholicity, such that the drugs were entrapped less easily.

Although specific embodiments have been illustrated and described, numerous modifications and variations are still possible without departing from the scope of the invention. The scope of the invention is limited by the accompanying claims.

The invention claimed is:

1. A method for producing elastic vesicles enveloping at least one hydrophilic active ingredient comprising:
   heating and uniformly mixing water and the at least one hydrophilic active ingredient until the at least one hydrophilic active ingredient completely dissolves in the water to form a water phase;
   lowering the temperature of the water phase;
   mixing a phospholipid and an edge activator in an oil phase, the phospholipid selected from the group consisting of phosphatidylcholine (PC), phosphatidylinostiol (PI), phosphatidvethanolamine (PE), and phosphatidic acid (PA);
   adding the oil phase to the water phase to accomplish pre-emulsification of the formulation of elastic vesicles; and
   miniaturizing or nanometerizing particles of the formulation of elastic vesicles to proceed with disruption and homogenization of the formulation such that elastic vesicles enveloping active ingredients are formed,
   wherein the method does not use organic solvents, and
   wherein the elastic vesicles are capable of transdermal delivery of the at least one active substance.

2. The method as claimed in claim 1, wherein the miniaturizing or nanometerizing step comprises placing the pre-emulsification into a nano high-pressure homogenizer to proceed with homogenization for 1-15 times, wherein the nano high-pressure homogenizer conducts the homogenization at a pressure up to 1500 bar, and wherein the nano high-pressure homogenizer includes a cooling tank operating at a temperature between 0 and 80 degrees Celsius.

3. The method as claimed in claim 1, wherein miniaturizing or nanometerizing comprises using an ultrasonic oscillation method.

4. The method as claimed in claim 1, wherein the at least one active ingredient is selected from the group consisting of substances for losing weight, whitening, anti-oxidation, anti-aging, and activating metabolism of cells.

5. The method as claimed in claim 1, wherein the edge activators are selected from the group consisting of silicon-containing edge activators, anionic edge activators, cationic edge activators, and nonionic edge activators.

6. The method as claimed in claim 3, wherein the phospholipid is phosphatidylcholine, wherein the edge activator is a silicon-containing edge activator.

7. The method of claim 6, wherein the weight percentage of the edge activator in the oil phase is 10% to 20%.

8. The method of claim 1, wherein the at least one active ingredient is caffeine.

9. The method of claim 5, wherein the silicon containing edge activator is selected from the group consisting of lauryl PEG/PPG-18/18 methicone, and PEG-12 dimethicone, and PEG/PPG-15/15 dimethicone.

10. The method of claim 5, wherein the anionic edge activator is selected from the group consisting of sodium lauryl sulfate, sodium lauryl ether sulfate, and disodium lauryl sulfosuccinate.

11. The method of claim 5, wherein the cationic edge activator is selected from the group consisting of ethyl trimethyl ammonium chloride and alkyl dimethyl benzyl ammonium chloride.

12. The method of claim 5, wherein the amphionic edge activator is selected from the group consisting of cocoamidopropyl betaine and sodium cocoamphoacetate.

13. The method of claim 5, wherein the nonionic edge activator is selected from the group consisting of cocamide MEA (cocoamide monoethanolamine), polysorbate 80, sorbitan monostearate, and steareth-2 (PEG-2 stearyl ether).

* * * * *